United States Patent [19]

Newberry, Jr. et al.

[11] Patent Number: 4,585,650

[45] Date of Patent: Apr. 29, 1986

[54] SKIN LUBRICATING COSMETIC COMPOSITION

[75] Inventors: Thomas E. Newberry, Jr., Longwood; Ralph R. Uhrmacher, Satellite Beach; Robert K. Arblaster, Altamonte Springs, all of Fla.

[73] Assignee: White Laboratories, Inc., Orlando, Fla.

[21] Appl. No.: 432,551

[22] Filed: Oct. 4, 1982

[51] Int. Cl.$^4$ .................... A61K 7/15; A61K 31/14
[52] U.S. Cl. .................................... 424/73; 514/642
[58] Field of Search ................... 424/329, 73; 514/642

[56] References Cited

U.S. PATENT DOCUMENTS

| | | | |
|---|---|---|---|
| 2,876,161 | 3/1959 | Gieschi | 424/73 |
| 3,103,466 | 9/1963 | Farkas | 424/180 |
| 3,429,964 | 2/1969 | Rieger | 424/73 |
| 3,715,942 | 2/1973 | Courtney | 424/73 |
| 3,818,105 | 6/1974 | Coopersmith et al. | 424/358 |
| 3,843,780 | 10/1974 | Michaels et al. | 424/73 |
| 3,852,417 | 12/1974 | McLaughlin | 424/73 |
| 4,186,114 | 1/1980 | Nakamura et al. | 252/536 |
| 4,298,494 | 11/1981 | Parslow et al. | 252/174.16 |

OTHER PUBLICATIONS

Ash and Ash, Formulary of Cosmetic Preparation p. 347.
85 Chemical Abstracts, 166487u, 1976.
92 Chemical Abstracts, 220543u, 1980.
94 Chemical Abstracts, 20244b, 1981.
94 Chemical Abstracts, 71207z, 1981.
94 Chemical Abstracts, 127150v, 1981.

*Primary Examiner*—Albert T. Meyers
*Assistant Examiner*—John W. Rollins, Jr.
*Attorney, Agent, or Firm*—Willian Brinks Olds Hofer Gilson & Lione

[57] ABSTRACT

Water-based cosmetic compositions for lubricating the skin for shaving. The cosmetic compositions constitute thin lotions and include a mixture of effective amounts of water, a gel former and binding agent, a gelling agent with skin conditioning properties and an emollient. Titanium dioxide may be used to import color to the cosmetic composition.

22 Claims, No Drawings

SKIN LUBRICATING COSMETIC COMPOSITION

FIELD OF THE INVENTION

This invention relates to new cosmetic products, compositions, and their preparation and use. More particularly, this invention relates to water-based cosmetic compositions for lubricating the skin, a method for producing such compositions and application of the composition for use as a shave composition.

BACKGROUND OF THE INVENTION

Cosmetics and creams used as preparations for "shaving" are well known. "Shaving" means, for the purposes of the description of the present invention, the severing or cutting off of hair close to the surface of the skin. Conventional cosmetic and cream preparations are used to lubricate the skin and soften the hair to be shaved to facilitate the shaving process.

Conventional shaving preparations have significant drawbacks. Usually soap-based, the conventional preparations provide lubrication and softening effect to the shaving area but make the shaving area susceptible to drying and chafing upon completion of the shaving process. The drying and chafing problems affect the entire shaved skin surface.

This problem is less critical when the shave cream is applied to toughened areas of skin that are shaved on a near daily basis, such as a man's beard. The problem is very critical, however, when drying shave preparations are used to meet a woman's less frequent shaving needs on areas where the skin is considerably softer, such as the legs and underarms. Conventional soap-based shave creams are unsuitable for use by women because the delicate skin that is shaved becomes dry, chafed and irritated.

It has now been found that cosmetic compositions adaptable for use as a shave composition suitable to the shaving needs of a woman can be produced by use of a product in the form of a lotion and containing a skin soften agent.

SUMMARY OF THE INVENTION

It is therefore an object of the present invention to provide a water-based cosmetic composition for lubricating the skin for shaving without drying the skin upon removal of the composition.

It is a further object of the invention to provide a method for producing a shave composition which will not impart dryness to the skin area to which it is applied.

It is another object of the invention to provide a method for shaving utilizing a cosmetic composition which will not dry or irritate the skin in the shaved area.

To achieve the objects in accordance with the purpose of the invention, as embodied and broadly described herein, the invention is a water-based cosmetic composition for lubricating the skin comprising a mixture of effective amounts of water, a gel former and binding agent, a gelling agent with skin conditioning properties and an emollient. In a more preferred embodiment of the invention, the water-based cosmetic composition for lubricating the skin comprises a mixture of water, hydroxypropyl guar, guar hydroxypropyltrimonium chloride, and methylgluceth-10. In a more preferred embodiment of the invention, the cosmetic composition further comprises titanium dioxide.

As embodied and broadly described herein, the invention also comprises a water-soluble shave composition comprising a mixture of effective amounts of water, a gel former and binding agent, a gelling agent with skin conditioning properties, and an emollient. In a more preferred embodiment of the invention the water-soluble shave composition comprises a mixture of effective amounts of water, hydroxypropyl guar, guar hydroxypropyltrimonium chloride and methylgluceth-10.

As embodied and broadly described herein, the invention also comprises a method of producing a shaving composition comprising the steps of admixing effective amounts of hydroxypropyl guar, a gelling agent with detergent action, methylgluceth-10, titanium dioxide, mineral oil, lanolin alcohol, aloe gel and octoxynol-9.

As embodied and broadly described herein, the invention also comprises a method of shaving comprising the steps of applying a shave composition comprising hydroxypropyl guar, guar hydroxypropyltrimonium chloride, and methylgluceth-10 to a hair-covered skin area; and removing the hair from the skin by any conventional shaving means, the shave composition serving as a skin lubricant.

It is to be understood that both the foregoing general and the following detailed description are exemplary and explanatory only are not intended to be restrictive of the invention as claimed.

DETAILED DESCRIPTION OF THE PREFERRED EMBODIMENTS

Reference will now be made in detail to the presently preferred embodiment of the invention, an example of which is included herein.

In accordance with the invention, the water-based cosmetic composition for lubricating the skin comprises water.

In further accordance with the invention, the water-based cosmetic composition for lubricating the skin comprises a gel former and binder agent. The gel former and binding agent usable according to the invention may be selected from cellulose gums, carbomers or magnesium aluminum silicate. The presently preferred gel former and binding agent is hydroxypropyl guar available from Celanese Plastics and Specialties Company as "Jaguar HP 60". Examples of other gel former and binding agents usable in the present invention are carboxymethyl cellulose, hydroxypropyl cellulose, hydroxyethyl cellulose, "Carbopol" and veegum. Preferably, the gel former and binding agent is present in an effective amount generally ranging from about 0.1 to 4.0, more preferably 0.1 to 3.0 percent of the total weight of the water-based cosmetic composition.

In further accordance with the invention the cosmetic composition comprises a gelling agent with skin conditioning properties. Gelling agents with skin conditioning properties usable according to the invention are substituted quanternary ammonium compounds including quaterniums, stearalkonium chloride, and preferably, guar hydroxypropyltrimonium chloride, which is a quaternary ammonium derivative of hydroxypropyl guar and which is also known as 2-hydroxy-3-(trimethylammonio) propyl ether chloride. See page 117 of the third edition of the Cosmetic Toiletry and Fragrance Association, Inc. Cosmetic Ingredient Dictionary. The guar hydroxypropyltrimonium chloride is available from Celanese Plastics and Specialties Company as "Jaguar C-13-S" or "Jaguar C-13-SD". "Jaguar C-13-SD" is more preferred because of its dispersability properties. The guar hydroxypropyltrimonium chloride component is preferably present in an effective amount generally ranging from about 0.01 to 1.00, more preferably, 0.01 to 0.05 percent of the total weight of the water-based cosmetic composition.

The hydroxypropyl guar and guar hydroxypropyltrimonium chloride components combine to provide a product in lotion form which has a lean or thin consistency and good solubility in water. Unlike other products which are not water-soluble enough to break-down during shaving and rinsing in the razor shaving process, the above components produce a lotion-type product having improved water-solubility. The product of the present invention breaks down and passes through a razor during shaving, thus, preventing the razor from clogging or skipping over certain areas of hair covered skin and leaving patches of hair. Further, owing to increased water solubility, the lotion of the present invention, rinses off a razor more easily and completely than conventional preparations to provide a clean, clog-free razor for continued smooth shaving.

In further accordance with the invention, the composition comprises an emollient. Preferred emollients of softening agents may be selected from polyethylene glycol ethers of methylglucose such as methylgluceth-10. Methylgluceth-10 conforms generally to the formula $$CH_3-C_6H_{10}O_5-(OCH_2CH_2)_nOH$$

where n has an average value of 10, and is commercially available as "Glucam E-10" from Amerchol Co. See page 168 of the third edition of the Cosmetic, Tolietry and Fragrance Association, Inc. Cosmetic Ingredient Dictionary. Preferably the methylgluceth-10 component is present in an effective amount, generally ranging from about 0.05 to 15.00, more preferably, 1.00 to 10.00 percent by weight of the total weight of the cosmetic composition. The addition of the methylgluceth-10 component softens the area to be shaved to leave the shaved area, such as legs, smooth and soft.

Preferred ranges for the cosmetic composition components are given according to the total weight of the composition with water as the predominant ingredient by weight. The range of the water component is from about 50 to 90, more preferably, 60–80, percent of the total weight of the composition. A minimum amount of water may be used to produce a concentrated cosmetic lotion and a maximum amount of water may be used to produce a dilute cosmetic composition. The total weight percentages for the other components will vary widely in view of these extremes. Thus, manipulation of the weight percent or the components is possible by varying the concentration of the water component without departing from the true scope and spirit of the invention.

In further accordance with the invention, the cosmetic composition comprises a coloring component. Preferred embodiments of the water-based cosmetic composition comprises an effective amount of color component such as a colorant or dye. The colorants or dyes usable in the invention include calcium carbonate, zinc oxide, FD&C certified dyes and pigments, iron oxide and preferably, titanium dioxide. The preferred dye, titanium dioxide, is available commercially as "Titanium Dioxide 3328" from Whittaker, Clark and Daniels. Preferably, the component of titanium dioxide is present in a range of from 0.05 to 5.00, more preferably, 1.00 to 3.00 percent by weight of the total weight of the composition.

The preferred dye, titanium dioxide, is added to give color to the water-based cosmetic composition during use. Titanium dioxide will not break down during application of the cosmetic composition to the skin area to the treated. Conventional dyes used in the cosmetic composition have a tendency to become transparent during application. Consequently, conventional dyes do not readily indicate to the user which areas have been covered with the composition and which areas have been shaved. Titanium dioxide provides a white color and thus permits the user of the lotion to observe the presence or absence of lotion at particular skin areas during the shaving process.

Preferred embodiments of the invention further comprise a wetting agent or humectant. The wetting agent or humectant helps to moisten the skin and hair area that is to be shaved to faciliate a smooth shave. As is known, moist hair is shaved with less effort. The wetting agent or humectant used in the present invention is preferably octoxynol-9 which is commercially available as "Triton X-100" from Rohm & Hass. Co. and which is defined on pages 187 to 188 of the Cosmetic, Toiletry and Fragrance Association, Inc. Cosmetic Ingredient Dictionary as being the ethoxylated alkyl phenol that conforms generally to the formula $$C_8H_{17}C_6H_4(OCH_2CH_2)_nOH$$

where n has an average value of 9. There are, however, many emulsifier detergents, humectants or wetting agents usable according to the invention, as may be determined without undue experimentation. The use of octoxynol-9 is merely to be regarded as an example of a suitable wetting agent.

The preferred embodiment also contains mineral oil and lanolin alochol which may be added as a mixture such as commercially available "Amerchol L-101" from Amerchol Co. The mineral oil and lanolin alcohol mixture provides additional lubrication properties to the product and a vehicle for dissolving and removing water insoluble agents. Other ingredients may be suitably substituted for the minerial oil/lanolin alcohol mixture, including emollient oils, "Petrolatum", vegetable oils, etc.

The preferred embodiment also contains an aloe derivative or extract such as aloe gel, commercially available as "Aloe Gel concentrate" from Terry Co. The addition of aloe provides soothing and healing effect for the treated skin area, particularly because aloe derivatives are natural healing agents capable of soothing and healing dry chapped and chafed skin.

Several other ingredients may be used to produce the preferred embodiment of the invention. A detergent type surfactants such as, alphaolefin sulfonate, commercially avaiable as "Witconate AOS 40%" from Witco Chemical Corp, is added to reduce the surface tension of and provide lubrication to the water-based cosmetic composition of the invention. The addition of the detergent type surfactants permits easier mixing of the components during preparation and use.

A buffer is added to adjust the pH of the water portion of the lotion to provide an optimum environment for preparation of the composition and subsequent treatment of the skin. The buffer used in the presently preferred embodiment is citric acid.

Other ingredients may be added to the cosmetic composition such as a preservative like DMDM hydantoin commercially available as "Glydant" from GLYCO Chemicals, Inc., or a fragrance. Further, ingredients may be utilized during the production process to facilitate advantageous production of the cosmetic composition of the invention. For example, sodium hydroxide pellets may be added to increase the initial pH of the batch solution, or an antifoaming agent may be added to disperse foam build-up.

In accordance with the invention, a shave composition is produced by admixing effective amounts of the above-mentioned components according to a suitable procedure. The example which follows provides a detailed procedure for preparing the preferred water-based cosmetic composition of the invention.

In accordance with the invention, the shaving process may be carried out by applying the shave composition, prepared from the components described above to a hair covered skin area. The hair is removed from the skin area by any conventional means such as a barber's razor or a double-edged safety razor, etc.

In summary, the shave composition serves as a lubricant for the skin, a moisturizer for the hair and a softening agent for the skin area permitting a close clean shave with a minimum of razor dragging or clogging. The preferred shave composition of the invention helps prevent irritation such as razor rash caused by the shaving process. The shave composition further moisturizes the skin to prevent the drying, chapping and chafing of skin that can be caused by shaving. The aloe component of the shave composition provides a soothing and healing effect to the shaved area. Overall the shave composition provides a method of shaving that simultaneously permits a smooth, close, and clean shave and leaves the shaved area feeling smooth, soft, and non-irritated.

EXAMPLE

The invention will now be illustrated by example, which in no way limits the scope of the present invention. In conjunction with the general and detailed descriptions above, the example provides further understanding of the present invention.

The following example illustrates the preparation of a water-based shaving composition from the following formulation:

| Ingredient | Percent by weight |
| --- | --- |
| Deionized Water | 73.244 |
| Sodium Hydroxide Pellets | 0.006 |
| Titanium Dioxide 3328 | 3.000 |
| Jaguar HP-60 | 1.110 |
| Jaguar C-13-SD | 0.090 |
| Glucam E-10 | 8.000 |
| Witconate AOS 40% | 8.000 |
| Aloe Gel Concentrate | 0.050 |
| Amerchol L-101 | 5.000 |
| Triton X-100 | 1.000 |
| Fragrance | 0.200 |
| Glydant | 0.300 |
|  | 100.000 |
| Citric Acid 10% solution (as needed to bring pH of 5.6–6.2) | Estimated; 0.025% |

The shave composition is prepared according to the following method and procedure:

The following special instructions and cautions are to be followed for successful preparation of the shave composition:

A. The batch must be made on one shift or on consecutive shifts. Do not leave a partially completed batch for an extended time or overnight before completion. Delay will result in a rejected batch that cannot be repaired.
B. Several steps are labeled "Do not stop at this point—proceed immediately to the next step." This instruction is critical to the success of the batch. Excessive delay may cause a rejected batch that cannot be repaired.
C. If the batch thickens before the addition of the Glucam E-10, it should be rejected since it cannot be repaired. DO NOT ADD GLUCAM TO A THICKENED BATCH. The resulting mixture will be unacceptable and extremely difficult to remove from a tank.
D. The batch may thicken after or during step 9 (infra). If so, it will be slightly gummy. Increase agitation speed as necessary to move the batch, but try to avoid adding air. It may be necessary to scrape down the propeller shaft. The gumminess will disappear when the final pH is adjusted down to 6.0.
E. If the batch is still thin before the final pH adjustment, this is also normal. The batch should thicken when the pH is adjusted to 6.0.

EQUIPMENT

Generally, any suitable mixing container and agitation means may be utilized to produce the cosmetic composition of the invention. It has been found that a stainless steel manufacturing tank equipped with a homo-mixer and propeller "lightning" agitation or sweep agitation (as known in the cosmetics art) can be successfully employed.

PROCEDURE

1. Read and follow the cautions and special instructions listed (A-E) above.
2. Meter cold water into a manufacturing tank. Carefully add sodium hydroxide and mix with rapid agitation until disolved. CAUTION: Sodium hydroxide is a caustic material. Wear goggles and gloves for this step. Avoiding splashing.
3. Take a sample of water for a pH check. The pH should be approximately 10.8–11.2.
4. If the pH is lower than specified, add additional sodium hydroxide until the pH falls within the above-noted range.
5. Begin rapid agitation with homo-mixer. Add "Titanium Dioxide 3328" to the batch. Mix with rapid agitation for one-half hour.
6. Add "Jaguar HP-60" and "Jaguar C-13-SD" to the batch and continue rapid agitation with homo-mixer. CAUTION: Wear goggles and dust mask until the ingredients are fully dissolved, approximately 15–20 minutes. CAUTION: DO NOT STOP AFTER THIS STEP. PROCEED IMMEDIATELY TO STEP #7. The batch should be water thin at this point. If this phase is mixed too long before the next addition, the ingredients will gel and the batch will thicken. If this happens, the batch cannot be completed successfully.
7. Discontinue homo-mixture agitation. Mix with moderate "lightning" agitation. Examine a small sample of the batch which should be water thin at this point.

8. Add "Glucam E-10" to batch and mix with moderate "lightning" agitation until uniform. Continue mixing until any foam disperses. If necessary add 0.01% or less of an antifoam agent to help disperse foam.

9. Add "Glucam E-10," "Witconate AOS 40%," Aloe gel concentrate, "Amerchol L-101," "Triton X-100," "fragrance A 60-307" (from Alphine Co.), and "Glydant" one at a time, in the order listed, mixing well after each addition. NOTE: The batch may thicken and become slightly gummy after the addition of "Glydant". Increase the agitation speed as necessary to move the product, avoiding air. Scrape agitator shaft as necessary. CAUTION: DO NOT STOP AFTER THIS STEP. Continue with pH adjustment in next step. The batch will become increasingly more difficult to agitate as it thickens before the pH adjustment.

10. Adjust pH to 5.5–6.2 using 10% Citric Acid solution. (Mix up recommended amount listed in formulation (supra) and add a portion at a time until the proper pH is reached.) Mix with "lightning" agitation as necessary and pump product from bottom to top for thorough mix.

The scope of the present invention is not limited by the description, examples and suggested uses herein, and modifications can be made without departing from the spirit of the invention. For example, the water-based cosmetic composition may be combined with other suitable ingredients for applications as a shaving lotion for hair covered areas of the body that are not normally subjected to shaving but for medicinal or health reasons require shaving. This application may include shavings for surgery to a particular area or shaving of parts of an athlete's body that requires the application of tape to provide support to a joint or to attach a particular pieces of equipment. Analogous to a woman's shaving needs, these infrequently shaved areas are more susceptible to irritation, chafing and drying from shaving and require the application of a shave composition that has improved skin treatment characteristics versus conventional shave compositions. Thus, it is intended that the present invention cover the modifications and variations of this invention provided that they come within the scope of the appended claims and their equivalents.

What is claimed is:

1. A water-based cosmetic composition for lubricating the skin for shaving consisting essentially of a mixture of effective amounts of water, from about 0.1 to about 4.0 percent by weight of a gel former and binding agent selected from the group consisting of cellulose gums and magnesium aluminum silicate, from about 0.01 to about 1.0 percent by weight of a quaternary ammonium gelling agent with skin conditioning properties, and from about 0.05 to about 15 percent by weight of an emollient.

2. A water-based cosmetic composition according to claim 1 further comprising an effective amount of titanium dioxide.

3. The water-based cosmetic composition according to claim 1, wherein said gel former and binding agent is hydroxypropyl guar, wherein said gelling agent is guar hydroxypropyltrimonium chloride, and wherein said emollient is methylgluceth-10.

4. A water-based cosmetic composition according to claim 3 further comprising an effective amount of titanium dioxide.

5. A water-based cosmetic composition according to claim 4, wherein the titanium dioxide component is present in an amount in the range of 0.05 to 5.00 percent by weight of the total composition.

6. A water-based cosmetic composition according to claim 3, wherein the hydroxypropyl guar component is present in an amount in the range of 0.1 to 3.0 percent by weight of the total composition.

7. A water-based cosmetic composition according to claim 3, wherein the guar hydroxypropyltrimonium chloride is present in an amount in the range of 0.01 to 0.05 percent by weight of the total composition.

8. A water-based cosmetic composition according to claim 3, wherein the methylgluceth-10 component is present in an amount in the range of 1.00 to 10.00 percent by weight of the total composition.

9. A water-based cosmetic composition according to claim 3 or 4 further comprising an effective amount of a wetting agent.

10. A water-based cosmetic according to claim 9 wherein said wetting agent is octoxynol-9.

11. A water-based cosmetic composition according to claim 3 or 4, further comprising an effective amount of lanolin alcohol.

12. A water-based cosmetic composition according to claim 3 or 4, further comprising an effective amount of mineral oil.

13. A water-based cosmetic composition according to claim 3 or 4, further comprising an effective amount of aloe gel.

14. A water-based cosmetic shaving composition consisting essentially of by weight a mixture of from about 0.1 to about 4.0 percent hydroxypropyl guar, from about 0.1 too about 1.0 percent hydroxypropyltrimonium chloride, from about 0.05 to about 15 percent methylgluceth-10, from about 0.05 to about 5.00 percent titanium dioxide, and effective amounts of mineral oil, lanolin, alcohol, aloe gel and octoxynol-9.

15. A water-based cosmetic composition according to claim 14 further comprising an effective amount of alpha olefin sulfonate.

16. A water-based cosmetic composition according to claim 14 or 15 further comprising an effective amount of citric acid.

17. A water-soluble shave composition consisting essentially of a mixture of water, from about 0.1 to about 4.0 percent by weight of a gel former and binding agent selected from the group consisting of cellulose gums and magnesium aluminum silicate, from about 0.01 to about 1.0 percent of a quaternary ammonium gelling agent with skin conditioning properties, and from about 0.05 to about 15 percent by weight of an emollient.

18. The water-soluble shave composition according to claim 17, wherein said gel former and binding agent is hydroxypropyl guar, wherein said gelling agent is guar hydroxypropyltrimonium chloride, and wherein said emollient is methylgluceth-10.

19. A water-soluble shave composition according to claim 17 or 18, further comprising an effective amount of titanium dioxide.

20. A water-soluble shave composition according to claim 18, further comprising an effective amount of titaniumm dioxide, mineral oil, lanolin alcohol, aloe gel, octoxynol-9, alpha olefin sulfonate, and citric acid.

21. A method of shaving comprising the steps of:
applying shave composition as set forth in claim 3 to a hair-covered skin area; and
removing said hair from said skin by any conventional shaving means, said shaving composition serving as a lubricant.

22. A method of producing a shave composition comprising the step of admixing from about 0.1 to about 4.0 percent by weight of hydroxypropyl guar, from about 0.1 to about 1.0 percent by weight of guar hydroxypropyltrimonium chloride, from about 0.05 to about 15 percent by weight of methylgluceth-10, and from about 0.05 to about 5.00 percent by weight of titanium dioxide with effective amounts of mineral oil, lanolin alcohol, aloe gel and octoxynol-9.

* * * * *

UNITED STATES PATENT AND TRADEMARK OFFICE
CERTIFICATE OF CORRECTION

PATENT NO. : 4,585,650
DATED : April 29, 1986
INVENTOR(S) : Thomas E. Newberry, Et Al.

It is certified that error appears in the above-identified patent and that said Letters Patent is hereby corrected as shown below:

In Column 1, line 41, "soften" should be "softening"
In Column 2, line 56, "quanternary" should be "quaternary"
In Column 2, line 62, after "Cosmetic" insert ","
In Column 4, line 7, "the" should be "be"
In Column 4, line 58, "avaiable" should be "available"

In Column 6, line 9, "point" should not be hyphenated
In Column 6, line 14, "before" should be "before"
In Column 6, line 20, "may" should be "may"
In Column 6, line 43, "cold" should be "cold"
In Column 6, line 58, "CAUTION" should be "CAUTION"
In Column 6, line 65, "the" should be "the"
In Column 6, line 66, "batch cannot be completed successfully" should be "batch cannot be completed successfully"
In Column 7, line 16, "CAUTION" should be "CAUTION"
In Column 8, line 32, "effictive" should be "effective"
In Column 8, line 67, "titaniumm" should be "titanium"

Signed and Sealed this

Thirtieth Day of September 1986

[SEAL]

Attest:

DONALD J. QUIGG

*Attesting Officer*     *Commissioner of Patents and Trademarks*